The signals (or spectra) from the plurality of sensing means are relayed to an appropriate processing system for the aforementioned interpretation and analysis to determine whether or not any of the gaseous species to which the trapping devices and sensors are selective is present, and if so to detect that presence and identify the gaseous species. (This is of course based on the signal output of the sensors as they come in contact with the gas being monitored; if the gas contains any of such gaseous species then one or more telltale signal output indications will be observed by the processing apparatus.)

The invention as previously described has as one of its principal and further advantages the ability to compensate for "drift" which is frequently exhibited by chemical sensors typically used to detect and identify the gaseous species generally of interest in these matters. By "drift" is meant a change in output signal from the sensing means resulting from the effects of temperature, pressure or other uncontrolled influences over a relatively long period of time. The problem of drift is somewhat endemic to the use of systems in which sensors are utilized to obtain chemical information about a gas to be monitored. The drift, or change in output signals, of those sensors over a relatively long period of time is significant if the detection and identification of chemical or gaseous species requires employment of signal outputs taken on a relatively long-term basis, since a component of any change in the signal can be due to extraneous drift phenomena and have nothing to do with detection of gaseous species to which the sensor is selective. This introduces inaccuracy. However, with the present invention sensor drift can be compensated for without sacrificing the other advantages of the invention. This is because the present invention is readily adapted to a mode in which the signal from the sensing means can be measured at a time when none of the trapping means is being subjected to release or desorption conditions, thereby to obtain a base signal corresponding to the absence of any gas species to be detected and identified. Shortly thereafter, when one of the means for trapping gas species is deliberately subjected to release (e.g., desorption) conditions another measurement of the output signal of the sensing means can be obtained before a sufficient amount of time has passed for the drift phenomenon to have introduced an extraneous change in the signal (not related to detection of a gas species) relative to the base signal. The time difference between measurement of the base signal and measurement of the output signal corresponding to passage of the gas containing any gaseous species desorbed from the trapping means subjected to desorption conditions is insignificant compared to the time required for the output signal of the sensing means to be affected by drift. By continually measuring the difference between a "fresh" base signal and a signal obtained shortly thereafter corresponding to sensor-contact with gas containing any gaseous species of interest desorbed from a trapping means subjected to release conditions, any change in signel due to a drift phenomenon over a long period of time is cancelled out, thus compensating for the drift and removing any inaccuracy which might otherwise be introduced by comparison of signals which are no longer normalized.

One of the principal and essential features of the present invention is that the output of all of the trapping devices employed in accordance with it is contacted with each and every of the sensing means utilized. This produces a spectrum of signals for interpretation based on the contact of all of the sensors with the output of each of the trapping devices during the time it is subjected to desorption (or other release) conditions. The amount of chemical information about constituents of the gas being monitored is dramatically increased by using this arrangement; the amount of chemical information about the gas being monitored is, as will readily be appreciated, a function not just of the number of sensors, but rather of the product of the number of sensors times the number of trapping devices, the output from each of which is contacted with each of the sensors. As will further be appreciated, the amount of chemical information which can be obtained with the system increases even more dramatically as the number of trapping devices and/or sensors is increased.

In connection with the foregoing, a particularly advantageous processing system with which to use the invention is a computerized pattern recognition processor. This type of processor is based on the utilization of a pattern recognition algorithm, the accuracy and reliability of which in analyzing the output of signals of the associated sensors is substantially increased with an increase in the amount of chemical information (e.g., the number and information content of signal spectra) received from such sensors. As discussed above, practice of the present invention increases the amount of chemical information which is yielded by the plurality of sensing means. Thus, use of the present invention in conjunction with pattern recognition techniques confers a high degree of accuracy and reliability in the detection and identification of any gaseous species of interest in the gas being monitored, without sacrificing other advantages over alternative systems as discussed previously.

Apparatus in accordance with the invention is depicted in FIGS. 1 and 2. FIG. 1 shows a system 10 for concentrating, detecting and identifying any gaseous species of interest (e.g., contaminants, toxic substances or the like) which may be present in a gas to be monitored, in this case ambient air. The system includes an ambient air inlet tube 12 which is connected to each of thin-walled tubes 14, 16, 18 and 20 (each tube is 2 cm in length and has an inside diameter of 0.25 mm and an outside diameter of 0.35 mm), in this case made of fused silica, and adapted for concentration and release (under appropriate conditions) of certain of the aforementioned gas species in accordance with the invention. Tubes 14, 16, 18 and 20 are packed with gaspermeable beds of powdered sorbent material 22, 24, 26 and 28, respectively. Additionally, each of tubes 14, 16, 18 and 20 is equipped with a thin film resistance heater 30, coated directly on the tube. Each of sorbent materials 22, 24, 26 and 28 is chosen so that its selectivity to gaseous species of interest which may be present in the ambient air differs from the selectivity to such species of the other three sorbent materials. Each of tubes 14, 16, 18 and 20 communicates with sensors 32, 34, 36 and 38 via tube 40. The sensors themselves are piezoelectric sensor components which are coated with sorbent materials; the sorbent: materials used in beds 22, 24, 26 and 28 correspond to the sorbent materials used in sensors 32, 34, 36 and 38, respectively. The compartment 42 in which the array of sensors 32, 34, 36 and 38 is housed communicates with pump 44 via tube 46. Pump 44 operates to ambient air into the system through inlet tube 12 and expels air which has already passed through the system at exhaust 48. As can be seen from lines 50, 52,

DETECTION OF DEFECTS ON STRUCTURES

BACKGROUND OF THE INVENTION

1. Field of the Invention

The present invention relates to a method for detecting defects in metal structures and welds.

Metal structures and welds are invariably subjected to stress and fatigue conditions which give rise to the development of cracks or breaks internally or on the surface. The problem of such defects whether internal or external is even more acute in under-water or sub-sea structures which have to contend additionally with problems of corrosion.

Hitherto magnetic particle inspection has been used extensively to detect such defects especially in metal structures under water. This method relies on the fact that when a metal is magnetised, iron particles will be attracted to any change of flux of that field such as that caused by a defect whether internal or external. A cluster of these magnetic particles around a defect is termed an "indication" in the art. If a fluorescent dye is impregnated on the iron particles to produce the so-called "magnetic ink", then any particle clusters formed can be inspected by their fluorescence e.g. under UV light.

In the case of under-water structures a record of the "indication" is normally produced by a diver who photographs the "indication". This method, although useful, fails to produce a three-dimensional profile of the affected or defective area of a structure. Moreover, the diver has to be trained in the techniques involving knowledge of magnetic fields and flux, the art of applying the magnetic ink, visual appreciation of the nature and the extent of the damage to the affected area of the structure and finally ultraviolet photography of the surface treated with the normally fluorescent magnetic ink. In addition such UV photography has of necessity to be carried out under cover of darkness.

The absence of a three-dimensional profile of the affected area of the structure reduces the ability of the experts scrutinising the UV photograph to assess the damage accurately. Moreover, the need to carry out UV photography under darkness reduces considerably the flexiblity of the operation.

2. Description of Related Art

In an article by R. Purdy in the Journal "Non-Destructive Testing", November 1968, pp 363-369 a replica technique for recording magnetic particle indications is described. However, Purdy found that cold curing rubbers took too long to cure, e.g. 12 hours, and resorted to heat curable resins such as PVC. GB-A-934116 describes the use of PVC for a similar purpose and also employs a heat curing process. The heat curing process, however, was unsuccessful with fluorescent inks as the plasticiser component of the PVC paste absorbed the dye. The problem of slow cure or heat application is even more acute for under-water uses.

SUMMARY OF THE INVENTION

It is an object of the present invention to device a method of producing three-dimensional profiles of the area of a structure which has actual or suspected damage, especially under-water which will not only enable the operation to be carried out during daylight hours but can also be achieved in a very short time.

Accordingly, the present invention is a method of producing a three-dimensional profile of a surface of a ferro- or para-magnetic structure, said method comprising (a) subjecting the surface to a magnetic flux;
(b) applying substantially uniformly on the surface magnetic particles which are visually distinct or are capable of being visually distinguished when superimposed on a fast curing, cold-cure impression material, whereby the magnetic particles rearrange into clusters under the influence of the flux;
(c) applying on the clusters so formed the impression material capable of being cured into a solid resilient cast, said cast having the ability to lift the clusters of the magnetic particles from the surface by entrapment without substantially disturbing or distorting the pattern of the cluster formation and being capable of removal from the surface after curing;
(d) curing the impression material into a solid resilient cast whereby the clusters of the magnetic particles are held in and/or on the cast, and finally
(e) removing the cast impregnated with the magnetic particles from the surface.

DESCRIPTION OF PREFERRED EMBODIMENTS

By "fast curing, cold cure impression material" is meant a material which under ambient conditions of temperature (4°-35° C.) and pressure is capable of achieving adequate cohesive strength to enable said material to be peeled clean off a surface on which it is applied within 30 minutes of application without recourse to any external source of heat. Such impression materials in the context of the present invention are the so-called liquid rubbers (also known as liquid reactive rubbers) which are capable of being cured under the influence of catalysts, setting agents, radiation and the like at ambient temperatures.

The surface of the structure which is actually damaged or suspected of damage may be of any shape or size. For instance it may be part of a pipe, tube, rod, cylinder etc of circular, triangular, rectangular or polygonal cross-section provided that it is ferromagnetic or paramagnetic. Thus the surface may be of iron, cobalt, nickel or some alloys thereof.

The magnetic particles should be visually distinct in a background of the fast curing, cold cure impression material on which it is superimposed. The visual distinction may be inherent in the magnetic particles used or may be induced by an external aid, e.g. by fixing thereto a dye which fluoresces in UV light. Thus, the magnetic particles may be used as such or after fixing thereto a UV fluorescent dye. The fluorescent dye may be fixed on the magnetic particles by impregnation or dispersion of the particles in a solution of the dye. Particles having a fluorescent dye affixed thereto are the so-called "magnetic inks" and such particles can be distinguished from the background impression material by exposure to UV light.

The magnetic ink is suitably particles of paramagnetic or ferromagnetic metal to which the fluorescent dye is fixed. Specific examples of such magnetic metal particles include inter alia iron, cobalt, nickel or magnetic alloys thereof. Specific examples of magnetic inks having the fluorescent dyes affixed thereto include inter alia materials which are commercially sold under trade names such as Magnaglo (Registered Trade Mark) and Lumor (Registered Trade Mark).

using a Supermix II, coaxail cartridge dispensive system (sold by Liquid Control Corp).

After 15 minutes the magnetic flux was removed, the Aquaprint was fully cured and the cured solid cast peeled off the surface of the weld cap.

On visual inspection of the cast under UV light it was found that the pattern of the clusters formed by the magnetic particles and representing the defect had been retained undistorted on the solid cast of Aquaprint.

EXAMPLE 2

An evaluation according to the procedure of Example 1 was carried out using MIGLO UWI (Registered Trade Mark) ink and with the test tank water temperature controlled at 15° C.

Omniflex fast set (a polysulphide rubber) was manually premixed according to the manufacturers instructions prior to application over the defective area. On removal after 45 minutes the undistorted pattern of magnetic particle clusters could be observed under UV light on the solid rubber cast.

EXAMPLE 3

An evaluation according to the procedure of Example 2 was carried out using Magnaglo 405 (Registered Trade Mark) ink and Impregum F (a polyether rubber) with the test tank water temperature controlled at 15° C. The solid rubber cast was removed from the surface after 20 minutes and shown under UV light to have retained undistorted the pattern of magnetic particle clusters.

EXAMPLE 4

An evaluation according to the procedure of Example 2 was carried out using Lumor 4X (Registered Trade Mark) ink and Reprosil (a silicon rubber) with the test tank water temperature controlled at 22° C. The solid rubber cast was removed from the surface after 25 minutes and shown to have retained undistorted the pattern of magnetic particle clusters.

EXAMPLE 5

An evaluation according to the procedure of Example 1 was carried out with the test tank water temperature controlled at 5° C. The solid cast of Aquaprint was removed after 15 minutes and shown to have retained undistorted the pattern of magnetic particle clusters.

EXAMPLE 6

Standard magnetic particle inspection was carried out in air at 20° C. on the sample weld of Example 1 using Lumor 4X (Registered Trade Mark) magnetic ink prepared according to the manufacturers instructions. Omniflex fast set (a polysulphide rubber) was manually premixed according to the manufacturers instructions prior to application over the defective area with the magnetic flux still in place. After 15 minutes the magnetic flux was removed and the solid rubber cast peeled off the weld surface.

Visual inspection of the cast under UV light showed that the pattern of clusters formed by the magnetic particles had been retained undistorted on the solid cast.

EXAMPLE 7

The procedure of Example 6 was followed using Lumor 4X (Registered Trade Mark) ink and Aquaprint dispensed from a Supermix II cartridge dispensing system. On removal from the weld surface after 15 minutes it was shown that the magnetic particle clusters had been retained undistorted on the solid cast.

EXAMPLE 8

The procedure of Example 6 was followed at an air temperature of 30° C. using Lumor 4X (Registered Trade Mark) ink and Reprosil (a silicone rubber). On removal from the weld surface after 15 minutes the magnetic particle clusters could be seen in UV light to have been retained undistorted on the cast.

EXAMPLE 9

The procedure of Example 6 was followed at an air temperature of 10° C. using Supramor 4 Black (Registered Trade Mark) ink and Impregum (a polyether rubber). On removal from the weld surface after 25 minutes it was shown under visible light that the magnetic particle clusters had been retained undistorted on the cast.

EXAMPLE 10

A node, consisting of 500 MM pipes welded into a cross, was suspended in a tank of water. A diver carried out magnetic particle inspection on the node using Lumor (Registered Trade Mark) magnetic ink and detected a stress crack under the influence of a magnetic flux induced thereon by magnetic coils.

With the magnetic coils still live, Aquaprint (a maleinised polybutadiene, Trade Mark Registration applied for) was applied evenly over the affected area of the node using a Supermix II coaxial cartridge dispensive system (sold by Liquid Control Corp).

When, after 10 minutes, the Aquaprint was fully cured into a solid, resilient cast, the magnetic coils were turned off and the cured cast peeled off the surface of the weld.

On visual inspection of the cast under UV light it was found that the pattern of clusters formed by the magnetic particles and representing the stress crack had been retained undistorted on the cured solid cast of Aquaprint.

I claim:

1. A method of producing a three-dimensional profile of a surface of a magnetic structure, said method comprising
    (a) subjecting the surface to a magnetic flux;
    (b) applying substantially uniformly on the surface magnetic particles whereby the magnetic particles rearrange into clusters under the influence of the flux;
    (c) applying on the clusters so formed a fast curing, cold cure impression material having a viscosity ranging from about 500–1,500 poise and capable of being cured into a solid resilient cast, said cast having the ability to lift the clusters of the magnetic particles from the surface by entrapment without substantially disturbing or distorting the pattern of the cluster formation and being capable of removal from the surface after curing;
    (d) curing the fast curing, cold cure impression material into a solid resilient cast whereby the clusters of the magnetic particles are held in and/or on the cast, and finally
    (e) removing the cast impregnated with the magnetic particles from the surface.

2. A method according to claim 1 wherein the magnetic particles used have affixed thereto a UV fluorescent dye.

3. A method according to claim 1 or 2 wherein the magnetic particles are selected from iron, cobalt, nickel and magnetic alloys thereof.

4. A method according to claim 1 or 2 wherein the magnetic particles are in the form of a suspension or dispersion in a liquid, in a particulate form and is capable of being spread uniformly on the surface.

5. A method according to claim 4, wherein the magnetic particles are in a semi-solid particulate form.

6. A method according to claim 4, wherein the magnetic particles are in a solid particulate form.

7. A method according to claim 1 or 2 wherein the fast curing, cold cure impression material is a liquid rubber.

8. A method according to claim 7 wherein the fast curing, cold cure impression material used is a liquid rubber selected from polysulphide rubbers, polyether rubbers, silicone rubbers and maleinised polybutadiene rubbers.

9. A method according to claim 2, wherein the dye is affixed to the magnetic particles by impregnation.

10. A method according to claim 2, wherein the dye is affixed to the magnetic particles by dispersion of the particles in a solution of the dye.

11. A method of producing three-dimensional profiles of defects on and/or damage to a surface of an under-water structure, said method comprising applying to the surface a fast curing, cold cure impression material having a viscosity ranging from about 500–1,500 poise and capable of being cured into a solid resilient cast, said cast having the ability to form a replica of the defect which remains undistorted when lifted off from the surface of the under-water structure, curing the applied impression material into a solid resilient cast and removing the cured cast as a three-dimensional profile of the defect and/or damage.

12. A method of producing a three-dimensional profile of a surface of a magnetic under-water structure according to claim 11, said method comprising
  (a) subjecting the surface to a magnetic flux;
  (b) appylying substantially uniformly on the surface magnetic particles whereby the magnetic particles rearrange into clusters under the influence of the flux;
  (c) applying on the clusters so formed the fast curing cold cure impression material having a viscosity ranging from about 500–1,500 poise and capable of being cured into a solid resilient cast, said cast having the ability to lift the clusters of the magnetic particles from the surface by entrapment without substantially disturbing or distorting the pattern of the cluster formation and being capable of removal from the surface after curing;
  (d) curing the fast curing, cold cure impression material so as to form the solid resilient cast in such a way that the clusters of the magnetic particles are held in and/or on the cast, and finally
  (e) removing the cast impregnated with the magnetic particles from the surface.

13. A method according to claim 11 or claim 12 wherein the fast curing, cold cure impression material is maleinised polybutadiene.

14. A method according to claims 1 or 12, wherein the structure is ferro-magnetic.

15. A method according to claims 1 or 12, wherein the structure is para-magnetic.

16. A method according to claims 1 or 12, wherein the particles are visually distinct.

17. A method according to claims 1 or 12, wherein the particles are capable of being visually distinguished when superimposed on the fast, cold curing impression material.

18. A method according to claim 1 or 11 wherein a cast of maleinised polybutadiene is cured using a setting agent selected from amines, polyols, amides, polyamides, alkanolamines and alkanolamides.

19. A method according to claim 18 wherein the setting agent is triethanolamine.

20. A method according to claim 18, wherein the setting agent is a salt of triethanolamine with a carboxylic acid.

21. A method according to claim 18, wherein the setting agent is a salt of triethanolamine with a carboxylic acid in admixture with polyols.

22. A method according to claim 1 or 11, wherein the material is cured using radiation techniques.

23. A method according to claim 1 or 11, wherein the material is cured by using catalysts.

24. A method according to claim 1 or 11, wherein the material is cured by using setting agents.

25. A method of producing a three-dimensional profile of defects on and/or damage to a surface of an under-water structure, said method comprising applying to the surface a fast curing, cold cure impression material having a viscosity ranging from about 500–1,500 poise capable of being cured into a solid resilient cast said cast having the ability to form a replica of the defect which remains undistorted when lifted off from the surface of the under-water structure, curing the applied impression material so as to form a solid resilient cast at a temperature ranging from about 4° C. to about 30° C. and over a period of time ranging from about 10 minutes to about 40 minutes and removing the cured cast as a three-dimensional profile of the defect and/or damage.

26. The method of producing a three-dimensional profile of a surface of a magnetic underwater structure claim 25, further comprising:
  (a) subjecting the surface to a magnetic flux;
  (b) applying substantially uniformly on the surface magnetic particles whereby the magnetic particles rearrange into clusters under the influence of the flux;
  (c) applying on the clusters so formed the fast curing, cold cure impression material having a viscosity ranging from about 500–1,500 poise and capable of being cured into a solid resilient cast, said cast having the ability to lift the cluster of the magnetic particles from the surface by entrapment without substantially disturbing or distorting the pattern of the cluster formation and being capable of removal from the surface after curing;
  (d) curing the fast curing, cold cure impression material so as to form the solid resilient cast at a temperature ranging from about 4° C. to about 30° C. and over a period of time ranging from about 10 minutes to about 40 minutes in such a way that the cluster of the magnetic particles are held in and/or on the cast, and finally
  (e) removing the cast impregnated with the magnetic particles from the surface.

* * * * *

UNITED STATES PATENT AND TRADEMARK OFFICE
CERTIFICATE OF CORRECTION

PATENT NO. : 4,759,211

DATED : July 26, 1988

INVENTOR(S) : Robert Longley-Cook

It is certified that error appears in the above-identified patent and that said Letters Patent is hereby corrected as shown below:

Col. 1, l. 61, "device" should read --devise--

Col. 3, l. 46, "malenised" should read --maleinised--

Col. 3, l. 67, "(MPDB)" should read --(MPBD)--

Signed and Sealed this

Twenty-eighth Day of February, 1989

*Attest:*

DONALD J. QUIGG

*Attesting Officer*      *Commissioner of Patents and Trademarks*